United States Patent [19]
Artusi et al.

[11] Patent Number: 5,201,825
[45] Date of Patent: Apr. 13, 1993

[54] STERILE ENVIRONMENT PACKAGING

[75] Inventors: Aldo Artusi; Reto Artusi, both of Trüllikon, Switzerland

[73] Assignee: Sulzer Medizinaltechnik AG, Winterthur, Switzerland

[21] Appl. No.: 841,148

[22] Filed: Feb. 25, 1992

[30] Foreign Application Priority Data

Mar. 1, 1991 [CH] Switzerland ............ 00631/91

[51] Int. Cl.$^5$ .............................. B65D 81/02
[52] U.S. Cl. .................. 206/523; 206/45.34
[58] Field of Search ............... 206/523, 45.34

[56] References Cited

U.S. PATENT DOCUMENTS

| 3,918,581 | 11/1975 | Scammon . | |
|---|---|---|---|
| 4,015,709 | 4/1977 | Millet | 206/523 X |
| 4,733,806 | 3/1988 | Sloop | 206/523 X |
| 4,884,684 | 12/1989 | Bernardin et al. | 206/523 X |

FOREIGN PATENT DOCUMENTS

| 002416 | 6/1979 | European Pat. Off. | 206/523 |
|---|---|---|---|
| A011062 | 6/1984 | European Pat. Off. . | |
| 1425844 | 12/1965 | France | 206/523 |
| 1451468 | 7/1966 | France | 206/523 |
| A838143 | 6/1960 | United Kingdom . | |
| 8606044 | 10/1986 | World Int. Prop. O. . | |

Primary Examiner—William I. Price
Attorney, Agent, or Firm—Townsend and Townsend

[57] ABSTRACT

With the invention is shown a sterile environment packaging for an oblong rigid body, which consists of a supporting shell (2) made of plastic which can be sealed with a film lid so that it is airtight, and which consists of support members (4) made from compressible foam. The support members (4) are attached at right angles to the longitudinal axis of the supporting shell (2) and in the direction of the lid with protrusions (6) into lateral pockets (7) of the supporting shell (2). The support members (4) at the top and at the base act as a partition (8) to prevent contact between the rigid body (1) in the direction of the longitudinal direction and the supporting shell (2). Central support members (9) for housing the rigid body comprise an opening (10) in the direction of the longitudinal axis of the supporting shell (2), and said opening is accessible via a slit (11) on the lid side.

9 Claims, 1 Drawing Sheet

STERILE ENVIRONMENT PACKAGING

BACKGROUND OF THE INVENTION

The invention relates to a sterile environment packaging for an oblong rigid body, which consists of a plastic supporting shell, which can be sealed with a film lid so that it is airtight, and which consists of compressible foam support members.

Packagings, such as yoghurt pots, which consist of a plastic supporting shell and an airtight sealable film lid, are known from the foodstuffs industry. Airtight packagings are also used in technology relating to sterile environments, and when packing rigid and sensitive bodies they have additional support members made from compressible foam which are supposed to protect the packaged product from knocks. Thus patent specification EP 0 111 062 shows a double packaging for endoprostheses which can be sterilized.

The use of this packaging technique for implants, which in joint prostheses consist of oblong rigid bodies, presents problems in that the implant should be supported in each direction, in that identification should be possible in the packaged state and in that during removal no foreign bodies at all, such as parts of support members, should be entrained directly by the operating area.

SUMMARY OF THE INVENTION

The invention takes these circumstances into consideration. The object of the invention is to create a sterile environment packaging for oblong and rigid bodies of varying sizes, which is impact-resistant on all sides, and which permits a sterile packaging and leaves a cohesive empty packaging after the removal of the rigid body. This object is achieved in accordance with the invention in that support members are attached at right angles to the longitudinal axis of the supporting shell and in the direction of the lid having protrusions into lateral pockets of the supporting shell, in that support members at the top and at the base acting as a partition prevent contact between the rigid body in the direction of the longitudinal axis and the supporting shell, and in that central support members for storing the rigid body in the direction of the longitudinal axis of the supporting shell each have one opening, which is accessible via a slit on the lid side.

The advantages of the invention are regarded as being that in the sterile region a single person can open the packaging without the risk of packaging material flying around and can grasp the rigid body and bring it into a working field.

DESCRIPTION OF THE PREFERRED EMBODIMENTS

In the figures is shown a sterile environment packaging for an oblong rigid body, which consists of a plastic supporting shell, which can be sealed with a foil lid so that it is airtight, and of support members made from compressible foam. The support members are attached at right angles to the longitudinal axis of the supporting shell and in the direction of the lid with protrusions into lateral pockets of the supporting shell. The support members at the top and at the base act as a partition to prevent contact between the rigid body in the direction of the longitudinal axis and the supporting shell. Central support members for housing the rigid body each comprise an opening in the direction of the longitudinal axis of the supporting shell, which is accessible via a slit on the lid side.

Figure 1:
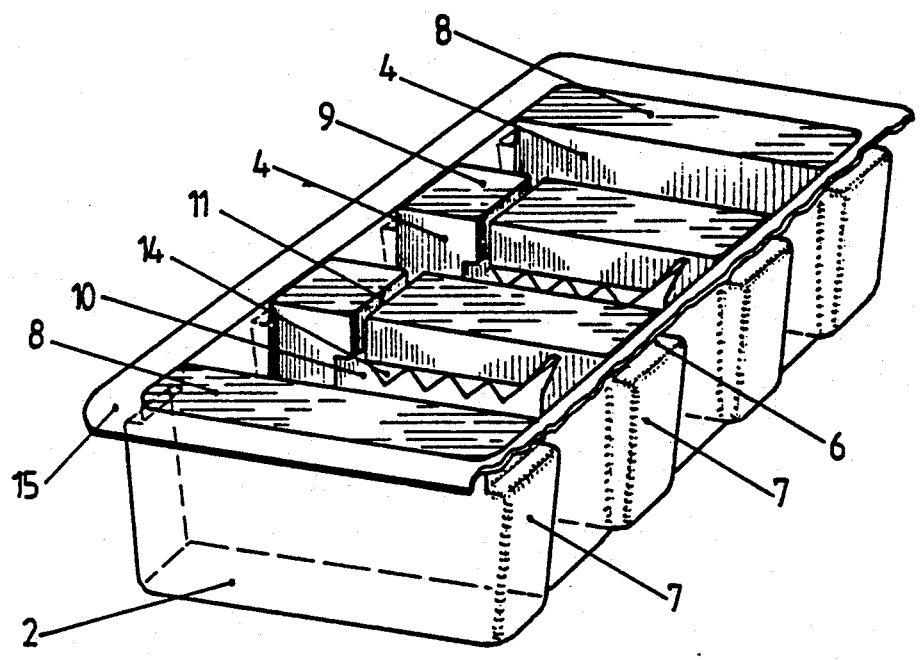
FIG. 1 is a perspective view of a supporting shell into which the support members are introduced to receive an oblong rigid body.
Figure 2:
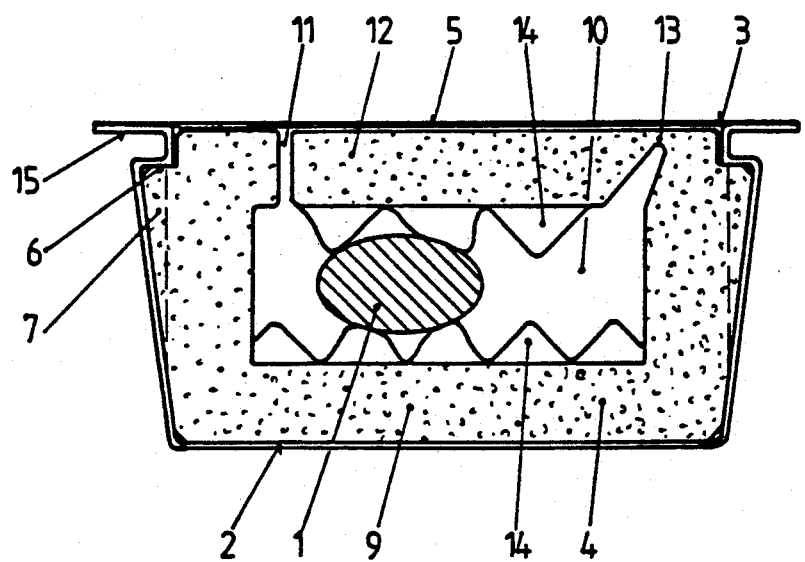
FIG. 2 is a cross section of a central support member through a sealed packaging.

In FIG. 1 is shown a supporting shell 2 having a rectangular surface area, which at the upper edge opens into a continuous collar 15 lying in one plane. The collar 15 is withdrawn laterally over the supporting shell 2 underneath it until mechanical sealing is possible by heat-sealing or gluing with a film lid 3. Support members 4 are inserted in the supporting shell 2 at right angles to the longitudinal axis of the rectangular surface, and they engage with protrusions 6 into lateral pockets 7 in the lateral walls of the supporting shell 2. The support members 4 at the top and at the base each form a partition 8 so as to prevent direct contact between the rigid body 1 in the direction of the longitudinal axis and the supporting shell 2, whereas central support members 9 for housing the rigid body 1 comprise an opening 10, which is accessible via a slit 11 on the lid side. As can be seen from FIG. 2, the central support members 9 form retaining flaps 12, which can be swung out towards the lid 5 and which extend between slit 11 and hinged joints 13, which are formed by a cross sectional reduction in the upper corners. To insert the rigid bodies, such as, for example, the shafts of hip joint prostheses, the retaining flaps 12 are swung out of the supporting shell 2. The resistance of the retaining flaps 12 against the swinging movement in the direction of the lid 5 is less than the resistance of the protrusions 6 against the detachment of the support members 4 from the supporting shell 2. After the introduction of the rigid body 1 the retaining flaps 12 are swung back and together with the collar 15 are covered by film lid 3. To connect the film lid 3 with the collar 15, firstly the film lid 3 and the retaining flaps 12 underneath are pressed together with a press (not shown) until the film lid 3 lies in the plane of the collar 15. The press keeps the film lid 3 in this position until the connection with the collar 15 has been effected. Heat-sealing or adhesion are suitable means of connection.

The rigid body 1 is larger than the openings 10, and this is compensated by an elastic deformation of the central support members 9 at the points of contact. At the same time frictional forces which prevent the rigid body 1 sliding are produced by clamping. The rigid body 1 is elastically suspended by the clamping effect. Shocks at right angles to the longitudinal axis are absorbed by the deformation of the central support members 9. So as not to stress excessively the clamping for shocks in the longitudinal axis, the support members designed at the top and at the base as partitions 8 and having varying wall thicknesses can be inserted into the supporting shell 2, so that the rigid body 1 is fixed in a form-locking manner in the longitudinal direction of the support shell 2 during insertion. The rigid body is therefore suspended elastically and in a shock-resistant manner on all sides, and there is no danger of it flying through vacuums and penetrating the supporting shell 2 in the event of a shock. So that it is possible to use central support members 9 for rigid bodies 1 having varying thicknesses, the openings 10 comprise inwardly directed protrusions 14, which enlarge the clamping region should the parts not be very thick. The protrusions 14 can be designed as ribs extending in the direction of the longitudinal axis or as cams protruding from the surface toward the interior. It is important that the foam of the support members does not comprise any loose or poorly attached particles which could be removed during the unpacking process. Closed-pore foams have proved to be useful in this connection. It is also advantageous if the position of the lettering on the rigid body 1 and the spaces between the support members 4 are adjusted so that with the use of transparent plastics for the supporting shell and the film lid 3 identification is possible in the packed condition. For handling and identification in a non-sterile region, the sealed sterile environment packaging is also packed so that it is sterile in a second packaging, e.g. in a transparent bag which can be torn open. Its transfer into the sterile working area to a person working in said sterile area, who pulls back the film lid 3 from the supporting shell 2 until the retaining flaps 12 and the rigid body 1 are uncovered, occurs after the bag has been ripped open.

For the better distribution of the forces in the sealed condition, which are transferred by clamping the central support members 9 onto the film lid 3, the film lid can have a more rigid pressure plate connected thereto on the inside in the covered region. After the removal of the rigid body there is always a cohesive empty packaging, so that the supporting shell 2 and the remainder of the packaging can always be retained with the same hand without interruption while the seal is ripped open, during removal and during the introduction of the rigid body 1 into a working area.

What is claimed:

1. A sterile environment packaging for an oblong rigid body comprising an elongated plastic supporting shell having a bottom, upright sides, upright ends and an open top, the sides defining on an inside of the shell sets of aligned, outwardly protruding pockets; a lid for closing and sealing the shell airtight; and support members made of compressible foam on the inside of the shell including protrusions extending into the pockets to position the support members transversely to the sides of the shell, the support members defining end support members engaging shell pockets proximate the shell ends and at least one central support member disposed in the shell and engaging shell pockets located intermediate the end support members, the central support member defining a central opening for receipt of the rigid body and including, on a portion of the central support member proximate the top opening, a slit to provide access to the opening, the end support member defining partitions between the rigid body in the opening and the ends of the shell preventing the rigid body from contacting the shell ends.

2. A packaging according to claim 1, wherein the central support member defines a retaining flap hingeably attached to a remainder of the central support member (9) and adapted to be folded back towards the lid (5) for the insertion and removal of the rigid member (1).

3. A packaging according to claim 2, wherein the resistance against hingeable movement of the retaining flaps (12) when withdrawing the rigid body (1) in the direction of the lid (5) is less than the resistance of the protrusions (6) against their removal from the pockets of the support members (4).

4. A packaging according to claim 2, wherein the retaining flaps (12) abut against the lid (3) and are biased against the rigid body (1).

5. A packaging according to claim 4, wherein the shell, the lid and the central support members are configured to exert a clamping force on the rigid body (1) when the lid is sealed to the shell.

6. A packaging according to claim 4, wherein the central support member comprises deformable protrusions (14) extending into the openings for producing a contact pressure on the rigid body (1).

7. A packaging according to claim 1, wherein the supporting shell (2) and the lid (3) are made form transparent plastic so that in the packed condition markings on the enclosed rigid body (1) are visible.

8. A packaging according to claim 1 including a plurality of spaced-apart central support members located intermediate the end support members.

9. A packaging according to claim 9 wherein the support member comprises closed-pore foam having clean exterior surfaces free of loose particles.

* * * * *